(12) United States Patent
Dennis et al.

(10) Patent No.: US 12,071,345 B2
(45) Date of Patent: Aug. 27, 2024

(54) SYSTEMS AND METHODS FOR PRODUCING SYNTHESIS GAS

(71) Applicant: Board of Regents of The University of Texas System, Austin, TX (US)

(72) Inventors: Brian H. Dennis, Austin, TX (US); Frederick M. MacDonnell, Austin, TX (US)

( * ) Notice: Subject to any disclaimer, the term of this patent is extended or adjusted under 35 U.S.C. 154(b) by 626 days.

(21) Appl. No.: 17/290,583

(22) PCT Filed: Oct. 30, 2019

(86) PCT No.: PCT/US2019/058916
§ 371 (c)(1),
(2) Date: Apr. 30, 2021

(87) PCT Pub. No.: WO2020/092610
PCT Pub. Date: May 7, 2020

(65) Prior Publication Data
US 2022/0002154 A1    Jan. 6, 2022

Related U.S. Application Data

(60) Provisional application No. 62/752,439, filed on Oct. 30, 2018.

(51) Int. Cl.
*C01B 3/38* (2006.01)
*B01J 19/00* (2006.01)
(Continued)

(52) U.S. Cl.
CPC ........... *C01B 3/382* (2013.01); *B01J 19/0013* (2013.01); *B01J 19/245* (2013.01); *B01J 21/12* (2013.01);
(Continued)

(58) Field of Classification Search
CPC .......... C01B 3/382; C01B 3/386; C01B 3/40; C01B 3/48; C01B 2203/0233; C01B 2203/0261; C01B 2203/0283; C01B 2203/085; C01B 2203/1058; C01B 2203/1082; C01B 2203/1282; C01B 2203/1671; C01B 2203/0894;
(Continued)

(56) References Cited

U.S. PATENT DOCUMENTS

2007/0000176 A1    1/2007   Liu et al.
2007/0217989 A1*   9/2007   Malhotra ............... B01J 8/067
                                                        423/437.1
(Continued)

OTHER PUBLICATIONS

Pina et al. Modeling and Simulation of an Autothermal Reformer. Latin American Applied Research. Jun. 20, 2006 [Retrieved Dec. 20, 2019] Retrieved from Internet URL: <https://pdfs.semanticscholar.org/149a/4c5dbfd75cf5b7228d4e0757793caed9b4cc.pdf>.
(Continued)

*Primary Examiner* — Andrew J. Oyer
(74) *Attorney, Agent, or Firm* — AdamsIP, LLC

(57) ABSTRACT

In some embodiments, a system for producing synthesis gas, the system including a reactor including a burner, a combustion chamber, and a catalyst chamber, and a mixer upstream of the reactor configured to mix fuel with steam to produce humidified fuel that is provided to the burner of the reactor.

16 Claims, 3 Drawing Sheets

(51) Int. Cl.
   *B01J 19/24* (2006.01)
   *B01J 21/12* (2006.01)
   *B01J 23/755* (2006.01)
   *C01B 3/40* (2006.01)
   *C01B 3/48* (2006.01)

(52) U.S. Cl.
   CPC .............. *B01J 23/755* (2013.01); *C01B 3/386* (2013.01); *C01B 3/40* (2013.01); *C01B 3/48* (2013.01); *B01J 2219/0009* (2013.01); *C01B 2203/0233* (2013.01); *C01B 2203/0261* (2013.01); *C01B 2203/0283* (2013.01); *C01B 2203/085* (2013.01); *C01B 2203/1058* (2013.01); *C01B 2203/1082* (2013.01); *C01B 2203/1282* (2013.01); *C01B 2203/1671* (2013.01)

(58) Field of Classification Search
   CPC ........ C01B 2203/142; C01B 2203/169; C01B 3/00; B01J 19/0013; B01J 19/245; B01J 21/12; B01J 23/755; B01J 2219/0009; Y02P 20/52; A61K 39/00
   See application file for complete search history.

(56) References Cited

U.S. PATENT DOCUMENTS

| | | |
|---|---|---|
| 2011/0263919 A1 | 10/2011 | West |
| 2017/0183227 A1 | 6/2017 | Finnerty et al. |
| 2017/0349434 A1 | 12/2017 | Bank et al. |

OTHER PUBLICATIONS

International Search Report, dated Apr. 19, 2021, for PCT Application No. PCT/US19/58916, filed Oct. 30, 2019.
Written Opinion of the International Searching Authority, dated Apr. 19, 2021, for PCT Application No. PCT/US19/58916, filed Oct. 30, 2019.

* cited by examiner

SYSTEMS AND METHODS FOR PRODUCING SYNTHESIS GAS

CROSS-REFERENCE TO RELATED APPLICATION

This application is a U.S. National Stage application of PCT Application Number PCT/US19/58916, filed on Oct. 30, 2019, which claims priority to U.S. Provisional Application Ser. No. 62/752,439, filed Oct. 30, 2018, which is hereby incorporated by reference herein in its entirety.

FIELD OF THE DISCLOSURE

The subject matter of the present disclosure refers generally to systems and methods for producing synthesis gas.

BACKGROUND

Synthesis gas, or syngas, is a gas mixture primarily comprising hydrogen ($H_2$) and carbon monoxide (CO). Syngas is typically a product of gasification and can be used in various applications, including electricity generation and liquid fuel production.

It is often desirable to produce syngas having a particular $H_2$:CO molar ratio. For example, an $H_2$:CO molar ratio of around 2:1 is typically considered desirable for liquid fuel production. It can be difficult, however, to consistently achieve a desired $H_2$:CO molar ratio given the various parameters involved in the process. Accordingly, it would be desirable to have systems and methods for producing syngas with which a desired $H_2$:CO molar ratio can be achieved with greater precision and consistency.

SUMMARY

In one aspect, a method of producing synthesis gas is provided. The method comprises generating steam and mixing the steam with a fuel gas, which is preferably natural gas, to produce humidified fuel and then combusting the humidified fuel and oxygen within a combustion chamber of a reactor to produce synthesis gas comprising hydrogen and carbon monoxide. The molar ratio of hydrogen to carbon monoxide in the synthesis gas may be precisely controlled by controlling the ratio of steam to fuel within the humidified fuel. An electric heater is utilized to generate the steam and to control the rate of steam generation, which thereby controls the steam-to-fuel ratio of the humidified fuel. The electric heater comprises a heating element disposed vertically within a pressure vessel. Water is pumped into a bottom of the pressure vessel, and power is supplied to the heating element such that a free surface is formed within the pressure vessel between a liquid water phase and a saturated steam phase. Steam is then output from the pressure vessel and mixed with the fuel gas to produce the humidified fuel that is delivered to the combustion chamber along with oxygen gas. The power supplied to the heating element may be adjusted to control the rate of steam generation from the pressure vessel.

In a preferred embodiment, water is pumped into the bottom of the pressure vessel using a positive displacement pump, which is preferably a diaphragm pump. This type of pump allows precise control of the water flow rate to the heater and thus precise control of the steam flow rate output from the pressure vessel. In one embodiment, the steam may be superheated by a portion of the vertical heating element that is disposed above the free surface within the pressure vessel.

In a preferred embodiment, the reactor further comprises a catalyst chamber coupled to the combustion chamber. The combustion reactants from the combustion chamber may react with a catalyst contained within the catalyst chamber to generate a gas mixture of hydrogen, carbon monoxide, unreacted methane, carbon dioxide, and water. In a preferred embodiment, the catalyst chamber includes a catalyst comprising nickel on an alumina-silica support.

The foregoing summary has outlined some features of the system and method of the present disclosure so that those skilled in the pertinent art may better understand the detailed description that follows. Additional features that form the subject of the claims will be described hereinafter. Those skilled in the pertinent art should appreciate that they can readily utilize these features for designing or modifying other structures for carrying out the same purpose of the system and method disclosed herein. Those skilled in the pertinent art should also realize that such equivalent designs or modifications do not depart from the scope of the system and method of the present disclosure.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have systems and methods for producing synthesis gas ("syngas") with which a desired hydrogen:carbon monoxide ($H_2$:CO) molar ratio, or syngas molar ratio, can be achieved with greater precision and consistency. Disclosed herein are examples of such systems and methods. In one embodiment, a system for producing syngas comprises means for precisely controlling the amount of water provided to a reactor of the system. This water is heated to create steam that is mixed with fuel, such as natural gas, to generate a humidified fuel that, along with oxygen, can be provided to the reactor for combustion and chemical transformation into syngas. By precisely controlling the amount of water used in the reaction, the $H_2$:CO molar ratio can be controlled with greater precision and consistency. In some embodiments, the humidified fuel is provided to the reactor at a temperature above the dew point but below the boiling point (e.g., 100° C.) of water. In some embodiments, $H_2$:CO molar ratios in the range of approximately 1.6:1 to 3:1 can be achieved.

In the following disclosure, various specific embodiments are described. It is to be understood that those embodiments are example implementations of the disclosed inventions and that alternative embodiments are possible. Such alternative embodiments include hybrid embodiments that combine features of different embodiments. All such embodiments are intended to fall within the scope of this disclosure.

Disclosed herein is a continuous process for producing syngas. As used herein, the terms "synthesis gas" and "syngas" refer to gas mixtures primarily comprising $H_2$ and CO. Such gas mixtures can also comprise other components, such as methane ($CH_4$), carbon dioxide ($CO_2$), and water ($H_2O$). Oxygen ($O_2$) gas and a humidified fuel, such as humidified natural gas, are continuously input into the system. As used herein, "oxygen gas" includes pure oxygen gas as well as gas that primarily comprises oxygen (at least 70% oxygen) but also includes one or more other types of gas, such as nitrogen. For example, the oxygen gas may comprise up to approximately 15% nitrogen by mole, which enables more economical generation of oxygen gas via air separation. The $H_2$:CO molar ratio is controlled by changing the amount of water used in the system and, more particularly, the fuel humidity. Increased humidity results in increased $H_2$:CO molar ratios. The process can generate molar ratios from 1.6:1 to 3:1.

Figure 1:
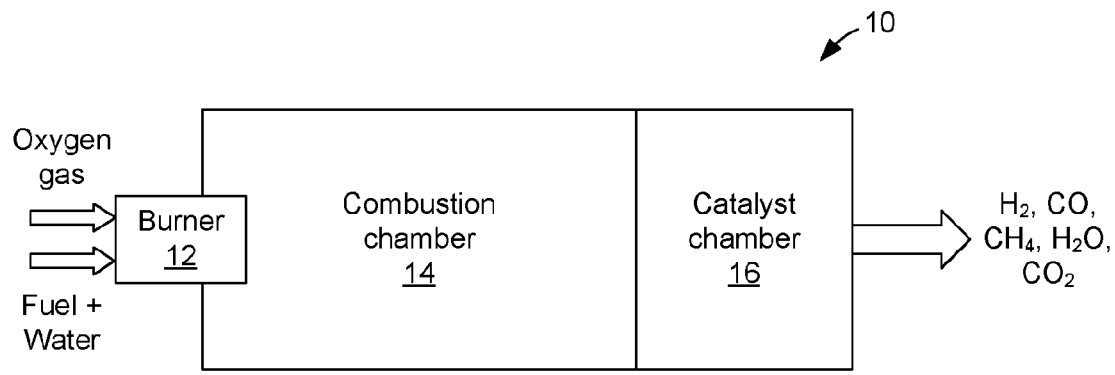
FIG. 1 is a schematic diagram of an embodiment of a syngas reactor.

FIG. 1 schematically illustrates a syngas reactor (or "reformer") 10 that can be used within a system for producing synthesis gas. The reactor 10 generally comprises a burner 12, a combustion chamber 14, and a catalyst chamber 16 that are arranged in series. The syngas production system can also include upstream components for preparing the reactants and downstream components for cooling the product gases, which are not identified in FIG. 1. The burner 12 is configured to combust the reactants (oxygen gas and the humidified fuel) within the combustion chamber 14 before they reach the catalyst chamber 16, in which they react with a catalyst contained therein to generate a gas mixture of $H_2$, CO, $CH_4$, $CO_2$, and $H_2O$. The composition of this gas mixture depends upon the burner design and the ratios of $O_2$ and $H_2O$ flow rates to fuel flow rate. In some embodiments, the volume flow ratio of oxygen gas to humidified fuel is in the range of approximately 0.5:1 to 0.6:1 to ensure that only a portion of the fuel product is reacted.

Figure 2:
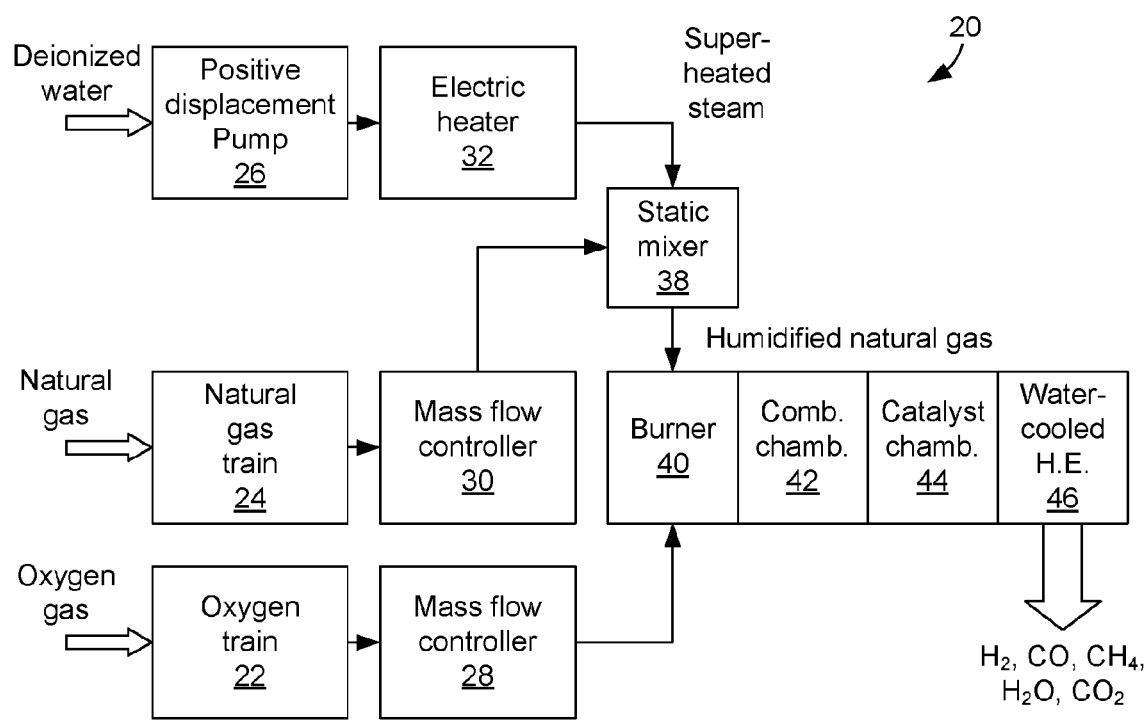
FIG. 2 is a schematic diagram of prototype system for producing syngas.

The reaction within the reactor 10 is exothermic and results in a significant temperature increase in the product gases as compared to the temperature of the incoming reactants. In some embodiments, the hot gases enter the catalyst chamber 16 at a temperature of approximately 900° C. to 1,300° C. In some embodiments, the catalyst comprises nickel (Ni) in an amount of approximately 7% to 9% weight loading on a alumina-silica support. An example alumina-silica composition is identified in Table 1 below.

ated to evaluate the effect of water on the syngas production process. As shown in FIG. 2, the system 20 comprised an oxygen train 22 that received oxygen gas, a natural gas train 24 that received natural gas, and a positive displacement pump 26 that received deionized water. The trains 22, 24 comprise supply systems including various pipes, valves, and pressure regulators that are used to control the flow and delivery of gas in industrial systems. Downstream of both the oxygen train 22 and the natural gas train 24 were separate mass flow controllers 28 and 30 that respectively controlled the flow of oxygen gas and natural gas to the remainder of the system 20.

Figure 3:
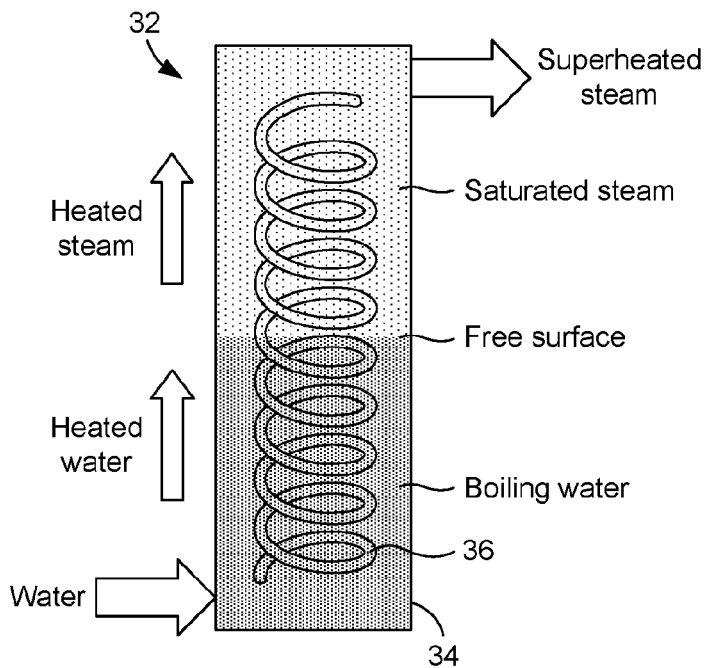
FIG. 3 is a schematic diagram of an electric heater that was used in the system of FIG. 2.

The deionized water was provided at room temperature to the positive displacement pump 26, which precisely controlled the volume of water input into the system 10. The pump 26 outputs a known volume of water with each pump cycle. The deionized water was pumped to an electric heater 32 that heated the water to produce superheated steam. FIG. 3 illustrates the configuration of the heater 32.

As shown in FIG. 3, the electric heater 32 comprised a stainless steel pressure vessel 34 that contained a vertically oriented coiled heating element 36. Deionized water was pumped into the bottom of the vessel 34 and heated until a stable free surface was formed that separates the liquid phase (boiling water) from the gas phase (saturated steam) of the water. The height of the free surface depended on the water flow rate and the power delivered to the heating element 36. The saturated steam produced by boiling within the heater 32 was further heated by the heating element 36, resulting in superheated steam. As the power was increased, the length of the exposed heating element increased and higher steam temperatures resulted.

A computer-based controller (not shown) was used to adjust the heater power as needed to achieve a desired outlet steam temperature for a given water flow rate. This was performed in a closed loop fashion using the outlet steam temperature as feedback. The controller used a lookup table that contained the minimum power required to bring incoming water at a known flow rate and known inlet temperature to boiling to set the minimum allowable power. The power can be increased by the controller beyond this minimum value in order to reach the desired steam temperature. The values in the table were calculated a priori using the known heat capacity of water and known heat losses from the heater.

In alternative embodiments, the required power can be experimentally determined by measuring the amount of heat power required to bring water to boiling at different inlet flow rates and inlet water temperatures. In still another

TABLE 1

| Chemical composition of the alumina-silica catalyst support. % mass | | | | | | |
|---|---|---|---|---|---|---|
| Alumina | Silica | Ferric Oxide | Titanium dioxide | Calcium Oxide | Magnesium Oxide | Alkalies ($Na_2O$ & $K_2O$) |
| 41.5 | 55.6 | 0.9 | 1.0 | 0.1 | 0.1 | 0.8 |

Syngas comprising $H_2$, CO, $CH_4$, $CO_2$, and $H_2O$ with a desired $H_2$:CO molar ratio exits the catalyst chamber 16. In some embodiments, the exiting syngas can have a temperature of approximately 600° C. to 1,000° C., but preferentially above 800° C.

FIG. 2 illustrates a prototype syngas production system 20 of the type described above that was constructed and operalternative, feedback to the controller can be obtained from a level sensor that measures the water level within the heater 32. By adjusting the heater power to maintain a given water level, the rate of steam generation will match the rate at which the liquid water enters the bottom of the heater 32. The temperature of the steam can then be controlled by establishing the level of the water relative to the heating element 36. A completely immersed heating element 36 would result in saturated steam, while a partially exposed element would result in some degree of superheated steam.

With reference back to FIG. 2, the natural gas from the mass flow controller 30 and the superheated steam from the electric heater 32 were supplied to and mixed within a static mixer 38 positioned upstream of a reactor (reformer), which comprised a burner 40, a combustion chamber 42, and a catalyst chamber 44. The temperature of the superheated steam was set such that the temperature of the mixture at the outlet of the static mixer 38 was above the dew point but below the boiling point (e.g., 100° C.) of water.

The humidified natural gas output from the static mixer 38 was delivered to the burner 40. The burner comprised a ¼ in. diameter tube concentrically positioned within a ⅜ in. diameter tube. Both tubes were made from 316 stainless steel. A catalyst comprising approximately 7% to 9% Ni placed on an alumina-silica support was used in the catalyst chamber 44 of the reactor. Syngas exiting the catalyst chamber 44 was then delivered to a water-cooled, tube-and-shell heat exchanger 46 that reduced the syngas temperature to room temperature. A gas analyzer (not shown) was then used to measure the molar composition of the dry syngas. Experiments were performed with and without the catalyst bed and for different ratios of water to fuel. The water produced by the reactions was calculated by mass balance.

The results in Table 2 show the partial oxidation reaction occurring in the combustion chamber 42 alone produced syngas with a molar ratio between 1.45:1 and 1.5:1. This ratio increased as the water-to-fuel ratio increased. The amount of $CO_2$ and $CH_4$ at the outlet of the combustion chamber also increased as the water-to-fuel ratio increased. The syngas molar ratio increased further after the gas mixture passed through the catalyst chamber 44. Table 2 shows a syngas molar ratio between 1.9:1 and 2.0:1 at the outlet of the catalyst bed, depending on the water-to-fuel ratio. Also shown in Table 2 are the mole fractions of the feedstock and products in the combustion chamber 42 and after passage over the catalyst bed within the catalyst chamber 44. Little change was observed in the $CO_2$ and $CH_4$ mole fraction between different water-to-fuel ratios. The percentage of fuel consumed by the reaction (Table 3) was also observed to be invariant with water-to-fuel ratio. However, higher water-to-fuel ratios resulted in greater fuel consumption in the catalyst bed and less consumption during the partial oxidation.

TABLE 3

Fraction of fuel consumed by each stage

| Fuel to Water Ratio | Fuel Consumed(%) | | |
|---|---|---|---|
| | Combustion | Catalyst | Total |
| 2.9 | 64 | 21 | 85 |
| 5.4 | 65 | 20 | 85 |

The overall process performed by the system 20 can be described as a partial oxidation reaction in series with chemical reactions occurring in the catalyst bed. The results show the impact of the water-to-fuel ratio on the partial oxidation reaction, resulting in increased $H_2$:CO molar ratios, increased $CO_2$, and increased $CH_4$ as the water is increased.

The chemistry in the catalyst bed can be interpreted as a set of competing chemical reactions:

Water-gas shift reaction (WGS):
$$CO + H_2O \leftrightarrow CO_2 + H_2$$

and

Steam-methane reforming reaction (SMR):
$$CH_4 + H_2O \leftrightarrow CO + 3H_2$$

Taking the output of the combustion chamber 42 as input to the above equations leads to a prediction of the catalyst chamber outlet composition that is within 3% of the measured values.

Table 4 shows the breakdown of the gas products as a function of each reaction. The results show the WGS reaction has a low overall contribution to the $H_2$ production, although this contribution increases as the water-to-fuel ratio increases. The SMR reaction produces a larger fraction of the syngas relative to partial oxidation at higher water-to-fuel ratios as well. Interestingly, the data shows the majority of $CO_2$ production occurs at partial oxidation.

TABLE 2

Molar flow rates and mole fractions for different water to fuel input ratios

| | Inputs | | | Combustion chamber output | | | | | Catalyst bed output | | | | |
|---|---|---|---|---|---|---|---|---|---|---|---|---|---|
| | (mol/hr) | | | (mol/hr) | | | | | (mol/hr) | | | | |
| Run | NG | $O_2$ | $H_2O$ | $CO_2$ | CO | $H_2$ | $CH_4$ | $H_2O$ | $CO_2$ | CO | $H_2$ | $CH_4$ | $H_2O$ |
| 1 | 72 | 48 | 25 | 10 | 38 | 57 | 26 | 63 | 12 | 52 | 104 | 11 | 46 |
| Xf | 0.5 | 0.33 | 0.17 | 0.05 | 0.20 | 0.29 | 0.13 | 0.32 | 0.05 | 0.23 | 0.46 | 0.05 | 0.20 |
| Xf water free | 0.6 | 0.4 | | 0.07 | 0.30 | 0.43 | 0.19 | | 0.06 | 0.29 | 0.58 | 0.06 | |
| 2 | 72 | 48 | 13 | 9 | 40 | 58 | 25 | 50 | 10 | 54 | 102 | 11 | 35 |
| Xf | 0.54 | 0.36 | 0.10 | 0.05 | 0.22 | 0.32 | 0.14 | 0.27 | 0.05 | 0.25 | 0.48 | 0.05 | 0.17 |
| Xf water free | 0.60 | 0.40 | | 0.07 | 0.30 | 0.44 | 0.19 | | 0.06 | 0.31 | 0.58 | 0.06 | |

TABLE 4

Fractions of products for each reaction.

| Water to Fuel Ratio | Fraction of Products Produced by Reaction (%) | | | | | | |
|---|---|---|---|---|---|---|---|
| | Partial Oxidation | | | Water Gas Shift | | Steam Methane Reforming | |
| | $CO_2$ | CO | $H_2$ | $CO_2$ | $H_2$ | CO | $H_2$ |
| 0.34 | 85 | 70 | 54 | 15 | 2 | 30 | 44 |
| 0.19 | 95 | 73 | 57 | 5 | 1 | 27 | 42 |

Overall, the results indicate that the humidity level of the fuel (e.g., natural gas) controls the $H_2$:CO molar ratio, the $CH_4$ content, and the $CO_2$ content. Therefore, precise control over the syngas molar ratio can be achieved with precise control over water (steam) and fuel flow rates.

Figure 4:
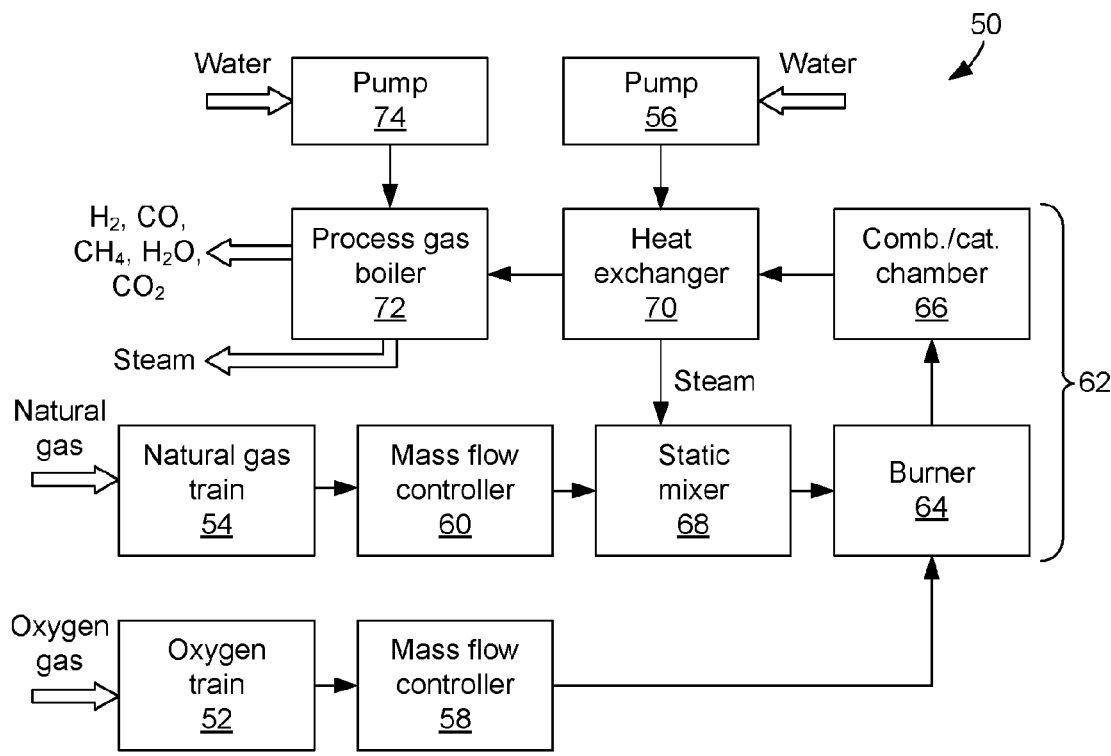
FIG. 4 is a schematic diagram of an embodiment of a first commercial-scale system for producing syngas.

A commercial-scale system for producing syngas was also designed. This system 50 is schematically illustrated in FIG. 4. The system 50 is designed to generate approximately 7,000 to 8,000 lb/hr of syngas having an $H_2$:CO molar ratio of approximately 2:1.

As shown in FIG. 4, the system 50, like the system 20, comprises an oxygen train 52 that receives oxygen gas, a natural gas train 54 that receives natural gas, and a first pump 56 that receives water. The first pump 56 can, for instance, comprise a positive displacement pump, such as a diaphragm pump. By way of example, oxygen can be supplied to the oxygen train 52 at a rate of 3,381 lb/hr and 37,912 scfh, natural gas can be supplied to the natural gas train 54 at a rate of 3,382 lb/hr and 67,700 scfh, and water is provided to the first pump 56 at a rate of 500 to 1,000 lb/hr (59-120 gph) at a temperature of 77° F. and 0 psig. Downstream of both the oxygen train 52 and the natural gas train 54 are separate mass flow controllers 58 and 60 that respectively control the flow of oxygen gas and natural gas to the remainder of the system 50. By way of example, the oxygen gas and natural gas can be provided to their respective mass flow controllers 58, 60 at 50 psig and the mass flow controllers can output the oxygen and natural gas at 6 psig and 10 psig, respectively.

As noted above, the amount of water provided to the reactor of a syngas production system is critical in controlling the $H_2$:CO molar ratio of the resulting syngas. This amount can be more precisely controlled using the pump 56 than by using a mass flow controller or other flow control mechanism. The water input into the first pump 56 is delivered by the pump to the heat exchanger 70 through which the high-temperature syngas produced by the reactor 62 also passes. In some embodiments, the heat exchanger 70 comprises metal pipes arranged vertically and perpendicular to the hot exhaust stream through which the water passes. The heat exchanger 70 heats the water to transform it into superheated steam that is delivered to a static mixer 68. By way of example, the steam can have a temperature greater than 600° F., a pressure of 10 psig, and a flow rate of 260 to 407 cfm.

Also like the system 20, the system 50 includes a reactor (reformer) 62 that comprises a burner 64 as well as a combustion chamber and catalyst chamber, which are together identified with reference numeral 66. Oxygen gas from the mass flow controller 58 is delivered to the burner 64 of the reactor 62. The natural gas from the mass flow controller 60, however, is delivered to the static mixer 68, in which the natural gas is mixed with the superheated steam to produce humidified natural gas that can then be input into the burner 64. By way of example, the humidified natural gas can be delivered to the burner at a pressure of 6 psig.

In some embodiments, the static mixer 68 comprises a straight pipe packed with structured mixing elements. Such a device enables continuous mixing of steam and natural gas and utilizes the energy of the flow to achieve a high degree of blending. By way of example, the static mixer 68 may comprise two mixing elements each 15 inches in length that experience approximately 4 psi of pressure drop at a combined natural gas and steam flow rate of approximately 4,400 lb/hr. This humidified natural gas can have a water-to-fuel mass ratio of approximately 1:10 to 1:1.5 and a temperature that is greater than the dew point but less than the boiling point (e.g., 100° C.) of water.

Syngas is produced by the reactor 62 that is output to the heat exchanger 70, as mentioned above. By way of example, the syngas can be output at 1818° F. and 0.6 psig. The syngas that exits the heat exchanger 70 (e.g., at 1,652° F. and 0.5 psig) can be passed through a process gas boiler 72 that is used both to decrease the temperature of the syngas and to generate steam from the waste heat of the system 50. Water for this steam production can be provided to the process gas boiler 72 using a second pump 74, which can also comprise a positive displacement pump. By way of example, the water can be provided to the second pump 74 at a rate of 9,148 to 9,777 lb/hr at 77° F. and 0 psig. The process gas boiler 72 can output syngas at 7,263 to 7,762 lb/hr, 86° F., and 0 psig, and can output steam at 9,148 to 9,777 lb/hr, 915° F., and 765 psia.

Figure 5:
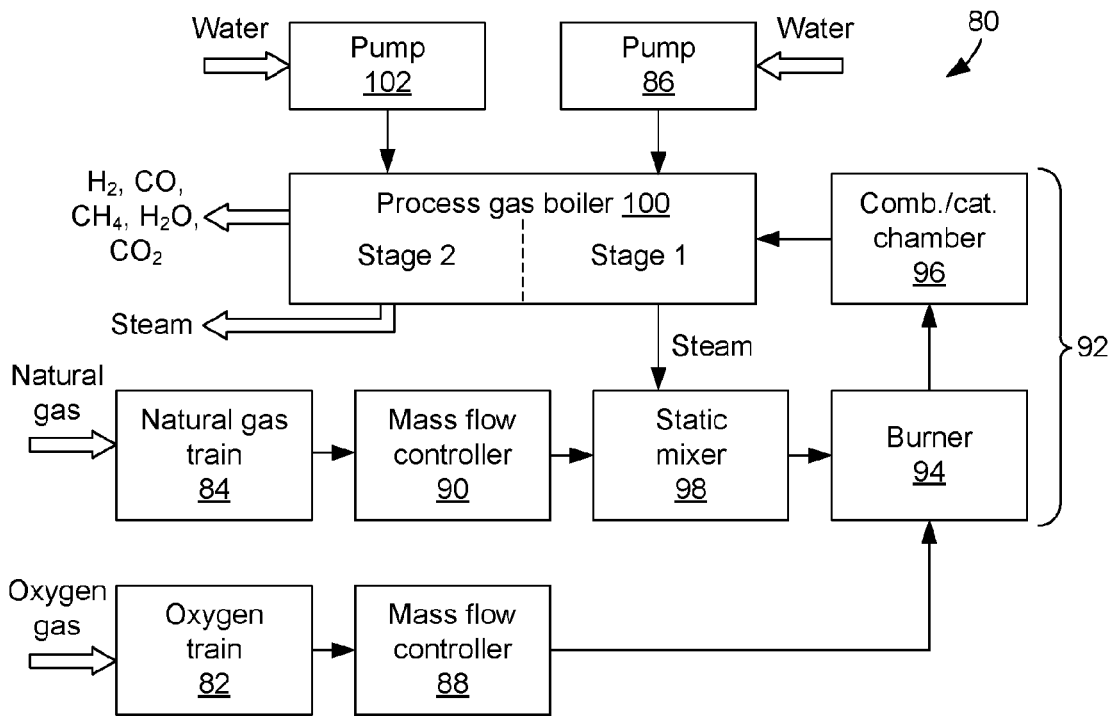
FIG. 5 is a schematic diagram of an embodiment of a second commercial-scale system for producing syngas.

FIG. 5 illustrates a further commercial-scale system 80 for producing syngas. This system 80 is similar in many ways to the system 50 described in relation to FIG. 4. As shown in FIG. 5, the system 80 comprises an oxygen train 82 that receives oxygen gas, a natural gas train 84 that receives natural gas, and a first pump 86 that receives water. By way of example, oxygen can be supplied to the oxygen train 82 at a rate of 3,381 lb/hr and 37,912 scfh, natural gas can be supplied to the natural gas train 84 at a rate of 3,382 lb/hr and 67,700 scfh, and water can be provided to the first pump 86 at a rate of 500 to 1,000 lb/hr (59-120 gph) at a temperature of 77° F. and 0 psig. Downstream of both the oxygen train 82 and the natural gas train 84 are separate mass flow controllers 88 and 90 that respectively control the flow of oxygen gas and natural gas to the remainder of the system 80. By way of example, the oxygen gas and natural gas can be provided to their respective mass flow controllers 88, 90 at 50 psig and the mass flow controllers can output the oxygen and natural gas at 6 psig and 10 psig, respectively.

The water input into the first pump 86 is delivered by the pump to a first stage of a process gas boiler 100 through which the high-temperature syngas produced by the reactor 92 also passes. This stage of the boiler 100 functions to exchange heat between the syngas and the water and, therefore, the boiler may also be considered and referred to as a heat exchanger. The process gas boiler 100 heats the water to transform it into superheated steam that is delivered to a static mixer 98. By way of example, the steam can have a temperature greater than 600° F., a pressure of 10 psig, and a flow rate of 260 to 407 cfm.

The system 80 further includes a reactor (reformer) 92 that comprises a burner 94 as well as a combustion chamber and catalyst chamber, which are together identified with reference numeral 96. Oxygen gas from the mass flow controller 88 is delivered directly to the burner 94 of the reactor 92. The natural gas from the mass flow controller 90, however, is delivered to the static mixer 98, in which the natural gas is mixed with the superheated steam to produce humidified natural gas that can then be input into the burner 94. By way of example, the humidified natural gas can be delivered to the burner at a pressure of 6 psig.

Syngas produced by the reactor 92 is output to the process gas boiler 100, as mentioned above. By way of example, the syngas can be output at 1818° F. and 0.6 psig. The syngas passes through the first stage and a second stage of the process gas boiler 100, which outputs the cooled syngas and steam. Water for this steam is provided to the second stage of the process gas boiler 100 using a second pump 102, which can also comprise a positive displacement pump. By way of example, the water can be provided to the second pump 102 at a rate of 9,148 to 9,777 lb/hr at 77° F. and 0 psig. By way of example, the syngas is output at 7,263 to 7,762 lb/hr, 86° F., and 0 psig, and the steam is output at 9,148 to 9,777 lb/hr, 915° F., and 765 psia.

Figure 6:
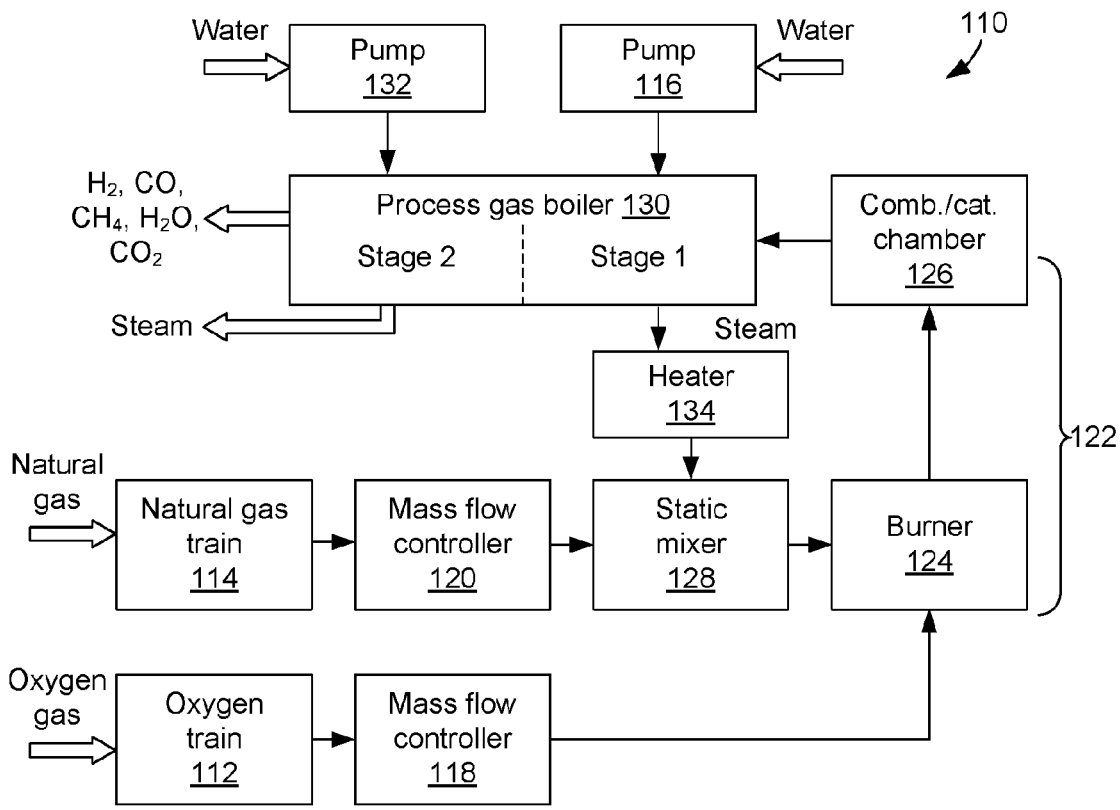
FIG. 6 is a schematic diagram of an embodiment of a third commercial-scale system for producing syngas.

FIG. 6 illustrates yet another commercial-scale system 110 for producing syngas. This system 110 is identical to the system 80 of FIG. 5, except the latter system further includes an electric heater 134 that receives steam at a first temperature and heats the steam to a second temperature prior to it being delivered to the static mixer 128. By way of example, the heater 134 can receive steam at 239° F. and raise its temperature to above 600° F. This superheated steam can then be provided to the mixer 128 at 10 psig and 260 to 407 cfm.

Like the system 80 shown in FIG. 5, the system 110 also comprises an oxygen train 112 that receives oxygen gas, a natural gas train 114 that receives natural gas, and a first pump 116 that receives water. Downstream of both the oxygen train 112 and the natural gas train 114 are separate mass flow controllers 118 and 120 that respectively control the flow of oxygen gas and natural gas to the remainder of the system 110. The water input into the first pump 116 is delivered by the pump to a first stage of a process gas boiler 130 through which the high-temperature syngas produced by the reactor 122 also passes. This stage of the boiler 130 functions to exchange heat between the syngas and the water and, therefore, the boiler may also be considered and referred to as a heat exchanger. The process gas boiler 130 heats the water to transform it into superheated steam that is delivered to the static mixer 128.

The system 110 further includes a reactor (reformer) 122 that comprises a burner 124 as well as a combustion chamber and catalyst chamber, which are together identified with reference numeral 126. Oxygen gas from the mass flow controller 118 is delivered directly to the burner 124 of the reactor 122. The natural gas from the mass flow controller 120, however, is delivered to the static mixer 118, in which the natural gas is mixed with the superheated steam to produce humidified natural gas that can then be input into the burner 124. Syngas produced by the reactor 122 is output to the process gas boiler 130, as mentioned above. The syngas passes through the first stage and a second stage of the process gas boiler 130, which outputs the cooled syngas and steam. Water for this steam is provided to the second stage of the process gas boiler 130 using a second pump 132, which can also comprise a positive displacement pump.

The invention claimed is:

1. A method for producing synthesis gas, said method comprising the steps of:
   providing a reactor comprising a combustion chamber;
   providing an electric heater comprising a heating element disposed vertically within a pressure vessel;
   generating steam using the electric heater, wherein the step of generating steam comprises: pumping water into a bottom of the pressure vessel, supplying power to the heating element such that a free surface is formed within the pressure vessel between a liquid water phase and a saturated steam phase, and outputting steam from the pressure vessel;
   mixing the steam output from the pressure vessel with a fuel gas to produce humidified fuel;
   controlling the ratio of steam to fuel of the humidified fuel by adjusting the power supplied to the heating element to control a rate of steam generation from the pressure vessel;
   delivering the humidified fuel and oxygen gas to the combustion chamber of the reactor; and
   combusting the humidified fuel and the oxygen gas to produce synthesis gas comprising hydrogen and carbon monoxide within the reactor.

2. The method of claim 1, wherein the humidified fuel has a mass ratio of steam to fuel in the range of 1:10 to 1:1.5.

3. The method of claim 1, wherein the synthesis gas has a molar ratio of hydrogen to carbon monoxide in the range of 1.6:1 to 3:1.

4. The method of claim 1, wherein a volume flow ratio of oxygen gas to humidified fuel is in the range of 0.5:1 to 0.6:1.

5. The method of claim 1, wherein the water is pumped into the bottom of the pressure vessel using a positive displacement pump.

6. The method of claim 5, wherein the positive displacement pump is a diaphragm pump.

7. The method of claim 1, wherein the steam output from the pressure vessel is superheated.

8. The method of claim 1, wherein the humidified fuel is at a temperature greater than the dew point of water but less than the boiling point of water.

9. The method of claim 1, wherein the humidified fuel is at a temperature of less than 100 degrees Celsius.

10. The method of claim 1, wherein the fuel gas comprises natural gas.

11. The method of claim 1, wherein the heating element is a coiled element.

12. The method of claim 1, wherein the step of mixing the steam with a fuel gas to produce humidified fuel comprises mixing the steam and fuel gas in a static mixer.

13. The method of claim 1, wherein the reactor further comprises a catalyst chamber coupled to the combustion chamber.

14. The method of claim 13, wherein combustion reactants from the combustion chamber react with a catalyst contained within the catalyst chamber to generate a gas mixture of hydrogen, carbon monoxide, unreacted methane, carbon dioxide, and water.

15. The method of claim 13, wherein the catalyst chamber includes a catalyst comprising nickel on an alumina-silica support.

16. The method of claim 15, wherein the catalyst comprises approximately 7% to 9% nickel by weight on the alumina-silica support.

* * * * *